US009414920B2

(12) United States Patent
Ozaki (10) Patent No.: US 9,414,920 B2
(45) Date of Patent: Aug. 16, 2016

(54) INSTRUMENT OF PATTERNING CUSP FOR CARDIAC VALVE RECONSTRUCTION AND COMPONENT THEREOF

(71) Applicant: Shigeyuki Ozaki, Tokyo (JP)

(72) Inventor: Shigeyuki Ozaki, Tokyo (JP)

( * ) Notice: Subject to any disclaimer, the term of this patent is extended or adjusted under 35 U.S.C. 154(b) by 465 days.

(21) Appl. No.: 14/070,706

(22) Filed: Nov. 4, 2013

(65) Prior Publication Data

US 2014/0058504 A1 Feb. 27, 2014

Related U.S. Application Data

(62) Division of application No. 12/758,844, filed on Apr. 13, 2010, now abandoned.

(51) Int. Cl.
*A61B 17/00* (2006.01)
*A61F 2/24* (2006.01)

(52) U.S. Cl.
CPC ............ *A61F 2/2445* (2013.01); *A61F 2/2415* (2013.01); *A61F 2/2496* (2013.01)

(58) Field of Classification Search
CPC ....... A61F 2/24; A61F 2/2412; A61F 2/2415; A61F 2/2442; A61F 2/2445; A61F 2/2448; A61F 2/2472; A61F 2/2496
USPC ...................................... 606/1; 623/2.1–2.42
See application file for complete search history.

(56) References Cited

U.S. PATENT DOCUMENTS

| | | | | |
|---|---|---|---|---|
| 5,163,955 A * | 11/1992 | Love | ...................... | A61F 2/2412 623/2.15 |
| 5,326,370 A * | 7/1994 | Love | ...................... | A61F 2/2412 606/167 |
| 5,415,667 A * | 5/1995 | Frater | .................... | A61F 2/2457 623/2.11 |
| 5,480,424 A * | 1/1996 | Cox | ...................... | A61F 2/0095 623/2.15 |
| 5,653,749 A * | 8/1997 | Love | ...................... | A61F 2/2412 128/898 |
| 5,662,705 A * | 9/1997 | Love | ...................... | A61F 2/2412 128/898 |
| 5,814,096 A * | 9/1998 | Lam | ...................... | A61B 5/1076 600/36 |
| 5,861,028 A * | 1/1999 | Angell | ................... | A61F 2/2412 623/2.11 |
| 5,928,281 A * | 7/1999 | Huynh | .................. | A61F 2/2409 623/2.14 |
| 6,129,758 A * | 10/2000 | Love | ...................... | A61F 2/2415 623/2.11 |
| 6,342,069 B1 * | 1/2002 | Deac | ...................... | A61F 2/2427 623/2.1 |
| 6,491,511 B1 * | 12/2002 | Duran | ................... | A61F 2/2415 425/394 |
| 6,517,576 B2 | 2/2003 | Gabbay | | |
| 6,582,419 B1 * | 6/2003 | Schoon | ................ | A61B 18/082 606/1 |
| 6,719,785 B2 | 4/2004 | Schoon et al. | | |

(Continued)

FOREIGN PATENT DOCUMENTS

| | | |
|---|---|---|
| JP | 2000-502937 | 3/2000 |
| JP | 2009-077838 | 4/2009 |
| WO | 97/25003 | 7/1997 |

*Primary Examiner* — William Thomson
*Assistant Examiner* — John R Downey
(74) *Attorney, Agent, or Firm* — Greenblum & Bernstein, P.L.C.

(57) ABSTRACT

In a case of repairing an aortic valve by forming a valve cusp with a biomembrane, the shape and the size of a valve cusp can be determined easily. An instrument including a valve cusp sizer for measuring the size of the valve cusp and a template for scribing lines for the shape of a valve cusp conforming to the measured size of the valve cusp, in which the valve cusp sizer has a plurality of differently-sized sizer blocks attached to each of the top ends of grip members respectively and each sizer block has an arcuate surface formed by cutting each of differently-sized circular cylinders at an angle conforming to the central angle for the commissure portions and, the template is formed with a scribing portion including a substantially semi-circular valve cusp base forming portion.

3 Claims, 8 Drawing Sheets

(56) References Cited

U.S. PATENT DOCUMENTS

| | | | |
|---|---|---|---|
| 7,819,915 B2* | 10/2010 | Stobie | A61F 2/2427 623/2.11 |
| 2002/0013621 A1* | 1/2002 | Stobie | A61F 2/2427 623/2.11 |
| 2002/0020074 A1* | 2/2002 | Love | A61B 5/1076 33/512 |
| 2002/0072794 A1* | 6/2002 | Gabbay | A61F 2/2412 623/2.12 |
| 2006/0195185 A1* | 8/2006 | Lane | A61F 2/2412 623/2.38 |
| 2008/0033544 A1 | 2/2008 | Lemmon | |
| 2010/0023119 A1* | 1/2010 | Yeo | A61F 2/2415 623/2.14 |
| 2010/0161046 A1* | 6/2010 | Marquez | A61F 2/2412 623/2.18 |
| 2011/0071622 A1* | 3/2011 | Fehling | A61F 2/2496 623/2.1 |
| 2011/0282440 A1 | 11/2011 | Cao et al. | |

* cited by examiner

INSTRUMENT OF PATTERNING CUSP FOR CARDIAC VALVE RECONSTRUCTION AND COMPONENT THEREOF

CROSS-REFERENCE RELATED APPLICATIONS

The present application is a divisional of U.S. application Ser. No. 12/758,844, filed Apr. 13, 2010, the disclosures of which are incorporated herein by reference in its entirety.

TECHNICAL FIELD

The present invention concerns an instrument for patterning a valve cusp and a component thereof, used for cardiac valve reconstruction that stitches a valve cusp formed of an artificial membrane or a biomembrane to a portion of a tricuspid cardiac valve such as an aortic valve from which an abnormal valve cusp has been excised. The instrument includes a valve cusp sizer for measuring the size of a valve cusp conforming to the size of a cardiac valve and a template for scribing lines of a valve cusp shape on an artificial membrane or a biomembrane conforming to the measured size of the valve cusp.

BACKGROUND ART

Figure 8:
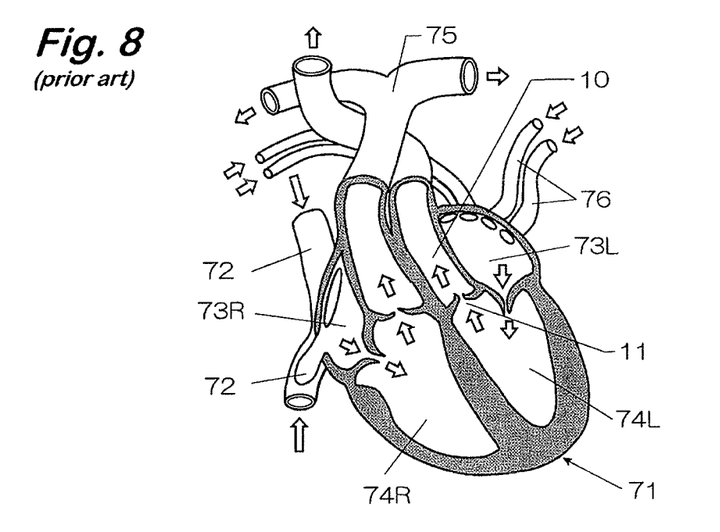
FIG. 8 is a schematic view of a heart.

As shown in FIG. 8, a heart 71 has a function of a pump that sends blood circulated through the body and flowing from superior and inferior vena cava 72, 72 into a right atrium 73R from a right ventricle 74R by way of a pulmonary artery 75 to right and left lungs and then delivers blood circulated from the lung by way of pulmonary veins 76 - - - to a left atrium 73L from the left ventricle 74L by way of an aorta 10 to the whole body.

Figure 9A:
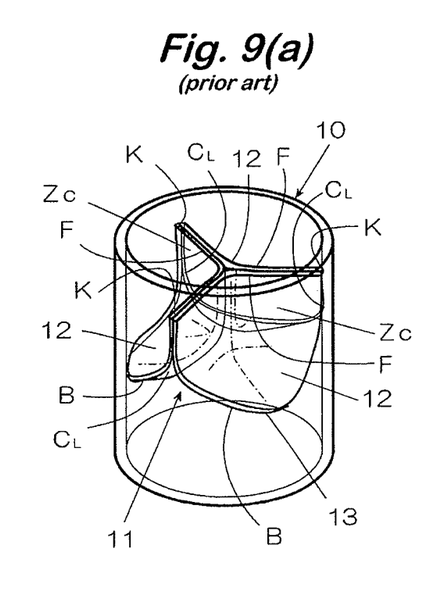
FIG. 9(a) is an explanatory view showing an aortic valve in a closed state.
Figure 9B:
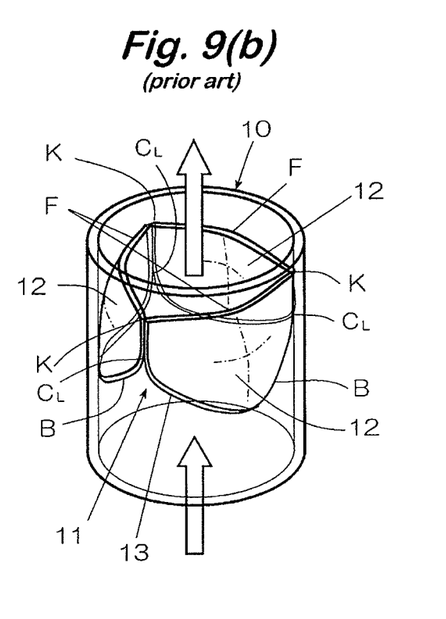
FIG. 9(b) is an explanatory view showing an aortic valve in an open state.

For example, an aortic valve 11 is a cardiac valve that is formed at the exit where the blood flows out from the left ventricle 74L to the aorta 10, in which cup-shaped three valve cusps 12, - - - of a thin membrane are present as shown in the schematic view of FIG. 9.

In each of the valve cusps 12, a portion defined along a commissure portion K of a cusp to a valve annulus on one end of a free margin F as an ON-OFF end→a bottom end $C_L$ of a coaptation zone just therebelow→a bottom B of the valve cusp→a bottom end $C_L$ of the other coaptation zone→a commissure portion K of a cusp to a valve annulus on the other end is integrated with the inner wall as valve annulus of the aorta 10 to constitute a fixed edge 13.

Then, along with dilation and contraction of the heart 71, since the pressure in the left ventricle 74L becomes negative during diastole, coaptation zones $Z_c$ formed on the side of the free margin F of the valve cusps 12 are jointed to each other to close the valve 11 as shown in FIG. 9(a), whereas since the pressure in the left ventricle 74L becomes positive during cardiac systole, the coaptation zones $Z_C$ of the valve cusps 12, 12, - - - are spaced apart from each other to open the valve 11 as shown in Fig. (b).

However, when atheriosclerosis, etc. proceed along with aging and calcium is deposited to calcify and harden the valve cusps, the valve cusps are restricted in their movement and do not open sufficiently, causing disease such as aortic valve stenosis.

According to the recent study, from 2 to 3% of the population of 26,000,000 aged 65 years or older in Japan suffer from the disease.

When the aortic valve stenosis is caused, since pressure loss is generated at the affected area, the left ventricle intends to maintain the blood pressure in the aorta at a normal 100 to 120 mmHg (during cardiac systole) contracts at a pressure higher than that (for example, 150 mmHg).

As a result, the left ventricle wall becomes thickened and causes hypertrophy and, when the thickness of the wall of the cardiac muscle is excessively increased, since the blood flow supplied from the coronary arteries is no more sufficient, the heart enters a hypoalimentation and insufficient oxygen state (miocardial ischemia). Particularly, if myocardial ischemia is caused when the oxygen demand is increased, for example, during activity, it may possibly cause symptoms such as chest pain and syncope.

In a case where the blood pressure difference exceeds, for example, 50 mmHg, this is judged as an indication that surgery is needed.

The most popularized treatment is valve replacement by using a prosthetic valve.

The prosthetic valve includes two types, that is, a mechanical valve formed of carbon, graphite, etc. and a heterogenic biovalve prepared from biomembranes of animals such as swinery and cattle and they are operated by the procedures as shown in FIG. 10.

That is, FIG. 10 is an explanatory view showing the outline of prosthetic valve replacement. As shown in FIGS. 10(a) to 10(b), all three valve cusps (left coronary cusp, right coronary cusp, noncoronary cusp) 79, - - - of the aortic valve situated at the inlet of the aorta 10 are excised while leaving only the valve annulus in contiguous from the left ventricle 74L to the aorta. Then, as shown in FIG. 10(c), the inner diameter of the aorta is measured by a sizer 81 as shown in FIG. 10(c) (refer to Patent document 1) and a prosthetic valve 82 having a valve annulus outer diameter equal with the inner diameter of the aorta is stitched to replace the valve.

[Patent Document 1] JP-T No. 2000-502937

Figure 10A:
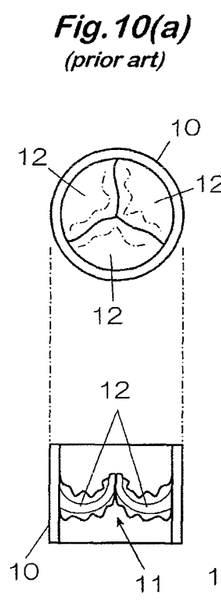
FIG. 10(a) is a view showing an aortic valve in which valve cusps are calcified.
Figure 10B:
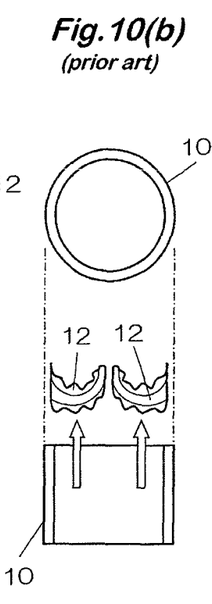
FIG. 10(b) is a view showing an aorta valve from which all valve cusps are excised.
Figure 10C:
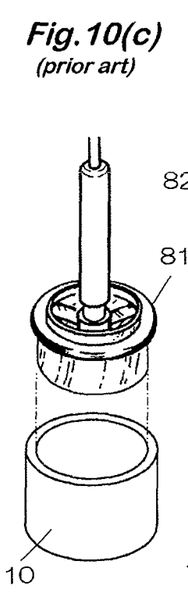
FIG. 10(c) is a view showing the state of measuring the inner diameter of an aortic valve by using an existent sizer.
Figure 10D:
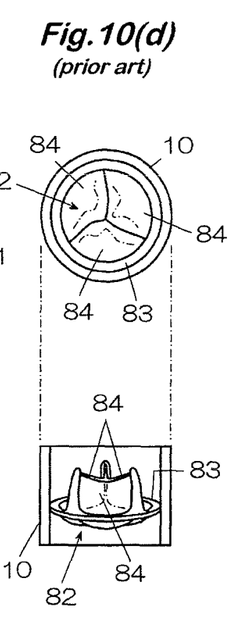
FIG. 10(d) is a view showing an aorta replaced with a prosthetic valve by existent aortic valve replacement.

However, even when replacement is conducted by the prosthetic valve 82, since the prosthetic valve 82 has a shape in which the valve cusps 84 - - - are attached to a valve annulus 83, when it is stitched to the aorta 10, the inner diameter of the aorta 10 is decreased by so as much as the thickness of the valve annulus 83 and the portion forms an orifice, causing pressure loss.

For example, in a case where the inner diameter of the aorta 10 is 20 mm, when a prosthetic valve 82 having the valve annulus 83 of 3 mm thickness is mounted as the prosthetic valve, the inner diameter of the prosthetic valve 82 is decreased to 14 mm even when it is opened fully and the area ratio is decreased to about 1/2. Then, a pressure loss is caused to the portion and although the valve is replaced with an aim of decreasing the pressure loss caused by aortic stenosis, the loss cannot be decreased sufficiently.

In a case of using a mechanical valve as the prosthetic valve 82, it is necessary to continuously take an anti-coagulant agent such as warfarin for for one's whole life, which results in a problem that it is difficult to arrest the bleeding in a case of injury, as well as, it is also pointed out a risk that teratogenesis may be caused possibly to a fetus when a pregnant woman takes the agent.

On the other hand, there is no requirement of taking warfarin in a case of using a heterogenic biovalve, but this involves a problem that the cost is as high as 1,000,000 yen or more per one valve unit.

Further, since both the mechanical valve and the heterogenic biovalve are foreign elements in the body, they may cause a risk of rejection.

Accordingly, as a result of an earnest study, the present inventor has established, instead of valve replacement, an aortic valve reconstruction of repairing an aortic valve by decalcifying hardened valve cusps by using a supersonic surgical aspirator, etc., thereby leaving valve cusps that can be used as much as possible, and forming only the valve cusp that is no more usable by using an autologuous biomembrane, etc.

In this case, when the valve cusp is formed by incising an autologuous pericardium, etc., since this comprises an autologuous biobody tissue, there is no problem of causing the rejection or blood clotting reaction (thrombus) and there is no requirement of purchasing an expensive prosthetic valve.

However, there has been a problem in this case how to cutout a valve cusp from a planar pericardium in the shape and the size conforming to the diameter of a patient's aorta.

It is considered that the diameter (or radius) of the valve annulus corresponds generally to the shape of the aorta. However, in a case of measuring the diameter, for example, by a sizer 81 used for attaching the prosthetic valve (refer to FIG. 10(c)), all valve cusps have to be excised. If a usable valve cusp is left, the valve cusp hinders measurement for the diameter of the aorta.

Figure 11:
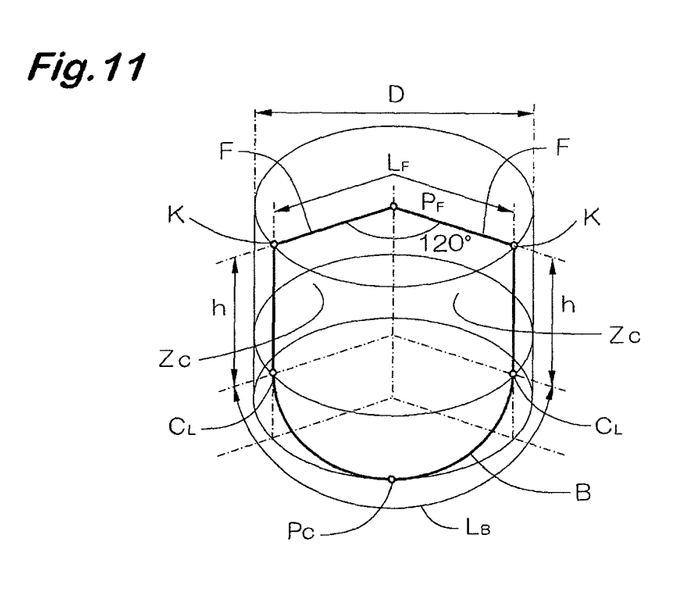
FIG. 11 is an explanatory view showing a model of a valve cusp.

Accordingly, the present inventor has attempted to use a model for the shape of the valve cusp based on the peripheral length of the valve cusp as shown in FIG. 11.

At first, assuming that an aorta is a circular cylinder having an inner diameter (diameter) D and that the central angle for a free margin $L_F$ extending from one commissure portion K of a cusp to a valve annulus, passing through the center $P_F$ of the aorta to the other commissure portion K of the cusp to the valve annulus (central angle for the commissure portions K, K) is 120° in a valve-open state, the length of the free margin is equal to D.

On the other hand, when assuming that the height from one commissure portion K to the bottom end $C_L$ of the coaptation zone $Z_C$ where the valve cusps are joined to each other as h (usually the height is considered sufficient if h=10 to 12 mm), the coaptation zone $Z_C$ has a rectangular shape having a width $L_F$ (=D) and a height h.

Since the central point $P_C$ for the base B of the valve cusp is at a position lower than the bottom end $C_L$ of the coaptation zone, the length $L_B$ for the base of the valve cusp extending from the bottom end $C_L$ of one commissure portion K, passing along the base of the valve cusp through the central point $P_C$ thereof to the bottom end $C_L$ of the other coaptation zone is larger than the inner peripheral length of the aorta having the central angle of 120°.

Then, when the shape of the valve cusp is formed as a semi-circular-square shape comprising a semi-circular cusp base portion having a length $L_B$ thereof up one-half circumference (=πr) of the inner periphery of an aorta and a rectangular portion corresponding to a rectangular coaptation zone $Z_C$ in contiguous therewith while making an allowance for stitching formed by cutting out a pericardium conforming to the shape and it is used for animal experiment of forming the prosthetic valve cusp of an aortic valve, it showed good result after surgery.

In this case, if it is possible to easily measure the inner diameter D of the aorta in a state of excising only one valve cusp, it is extremely convenient since the aortic valve can be formed while preparing the valve cusp by cutting out the pericardium during surgery.

DISCLOSURE OF THE INVENTION

Subject to be Solved by the Invention

The present invention has been achieved based on the inventor's finding as described above and, it intends to easily determine the shape and the size of a valve cusp in a case of treating a tricuspid cardiac valve such as an aortic valve by replacing only the valve cusp that can no more be used with an autologuous biomembrane or the like, thereby reconstructing the aortic valve.

Means for Solving the Subject

The present invention provides an instrument of patterning a valve cusp used for aortic valve reconstruction by stitching a valve cusp patterned from an artificial membrane or a biomembrane to a portion of a tricuspid cardiac valve such as an aortic valve from which an abnormal cusp has been excised, the instrument including;

a valve cusp sizer for measuring the size of a valve cusp conforming to the size of a cardiac valve, and a template for scribing lines of the shape of the valve cusp on the artificial membrane or the biomembrane conforming to the measured size of the valve cusp, in which the valve cusp sizer has a plurality of differently-sized sizer blocks for measuring the length of a valve annulus extending from one commissure portion of a valve cusp to a valve annulus to the other commissure portion of the valve cusp to the valve annulus of an excised valve cusp, where each of the seizer blocks is attached to each of the top ends of grip members respectively and each of the sizer blocks has an arcuate surface formed by cutting each of differently-sized circular cylinders at an angle conforming to the central angle for the commissure portions and, the template is formed with a scribing portion including a substantially semi-circular valve cusp base forming portion having a diameter as a sum of a nominal diameter defined for a diameter of a circular cylinder constituting the arcuate surface of a sizer block whose arcuate surface conform at both ends thereof to both of the commissure portions of the excised valve cusp when the cusp sizer is inserted to a valve annulus from which the valve cusp has been excised and an allowance for stitching margins, and a coaptation zone forming portion in contiguous with the valve cusp base forming portion.

Effect of the Invention

According to the invention, the valve cusp sizer is inserted to the valve annulus in a state of excising an abnormal valve cusp of a tricuspid cardiac valve such as an aortic valve and, when the diameter of the sizer block whose arcuate surface conform at both ends thereof to the commissure portions of the excised valve cusp, the diameter is defined as a nominal diameter, and this is used as an index for deciding the size of the valve cusp.

Since the scribing portion conforming to the nominal diameter is formed in the template, when a biomembrane, for example, a pericardium is extended, the template is put thereon, the shape of the a valve cusp is drawn along the scribing portion by using, for example, a sterilized surgery skin marker, etc. and then the biomembrane is excised along the line, a prosthetic valve cusp conforming to the shape of the excised valve cusp is formed.

Then, when the thus formed prosthetic valve cusp is directly stitched to the valve annulus where the base of the excised valve cusp has been joined, a tricuspid cardiac valve such as an aortic valve can be formed without decreasing the valve annulus thereof.

PREFERRED EMBODIMENTS OF THE INVENTION

The present invention intends to easily determine the shape and the size of a valve cusp in a case of reconstructing, a tricuspid cardiac valve such as an aortic valve by replacing only the valve cusp which is no more usable using, an autologuous biomembrane, etc.

For this purpose, an instrument of patterning a valve cusp used for aortic valve reconstruction by stitching a valve cusp patterned from an artificial membrane or a biomembrane to a portion of a tricuspid cardiac valve such as an aortic valve from which the abnormal cusp has been excised includes;

a valve cusp sizer for measuring the size of a valve cusp conforming to the size of a cardiac valve, and a template for scribing lines of the shape of the valve cusp on the artificial membrane or the biomembrane conforming to the measured size of the valve cusp.

The valve cusp sizer has a plurality of differently-sized sizer blocks for measuring the length of a valve annulus extending from one commissure portion of a cusp to a valve annulus to the other commissure portion of the cusp to the valve annulus of an excised valve cusp, where each of the seizer blocks is attached to each of the top ends of grip members respectively and each of the sizer blocks has with an arcuate surface formed by cutting each of differently-sized circular cylinders at an angle conforming to the central angle for the commissure portions.

The template is formed with a scribing portion including a substantially semi-circular valve cusp base forming portion having a diameter as a sum of a nominal diameter defined as a diameter of a circular cylinder constituting the arcuate surface of a sizer block whose arcuate surface conform at both ends thereof to both of the commissure portions of the excised valve cusp when the cusp sizer is inserted to a valve annulus from which the valve cusp has been excised and an allowance for stitching margins, and a coaptation zone forming portion in contiguous with the valve cusp base forming portion.

First Embodiment

Figure 1:
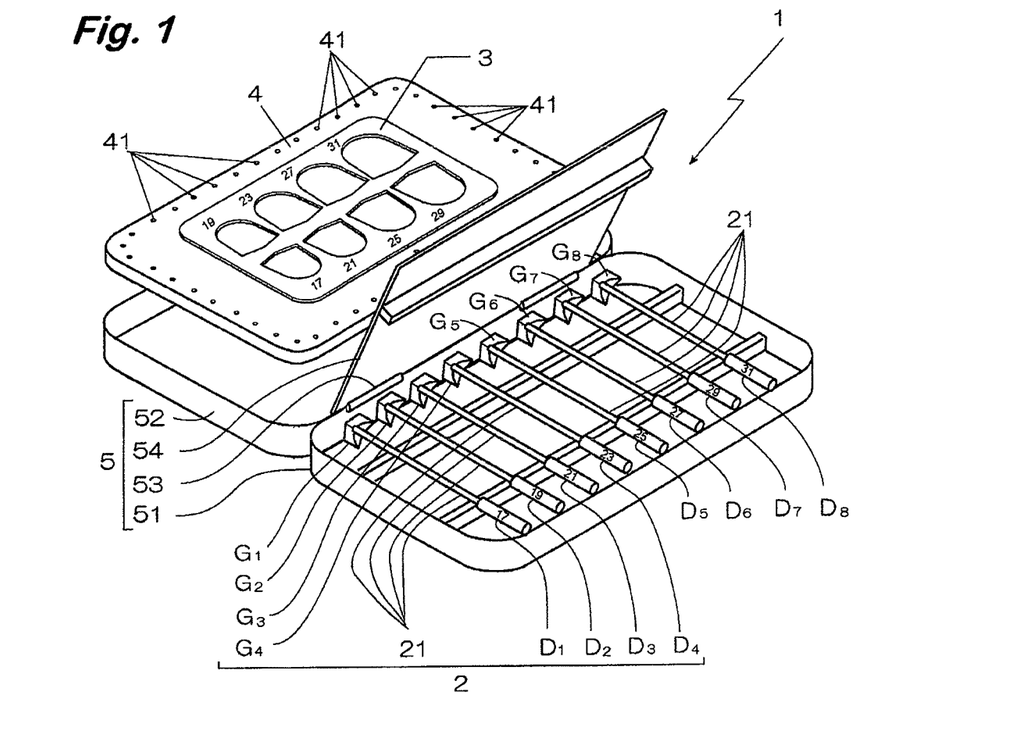
FIG. 1 is an explanatory view showing an example of a valve cusp forming instrument according to the invention.

FIG. 1 shows an instrument 1 of this embodiment which includes a valve cusp sizer 2 for measuring the size of a valve cusp conforming to the size of a cardiac valve, a template 3 for scribing lines of a shape of the valve cusp on an artificial membrane or a biomembrane conforming to the measured size of the valve cusp, and a base plate 4 for maintaining the artificial membrane or the biomembrane in a planar state upon scribing the lines for the shape of the cusp by using the template 3.

The valve cusp sizer 2, the template 3, and the base plate 4 are contained in a stainless steel case 5, and they can be sterilized in a state as they are contained therein by an sterilizing autoclave.

In the case 5, a main body 51 for containing the valve cusp sizer 2, and a cover 52 for containing the template 3 and the base plate 4 are opened and closed by a hinge 53, and a partition plate 54 is disposed therebetween.

Figure 2:
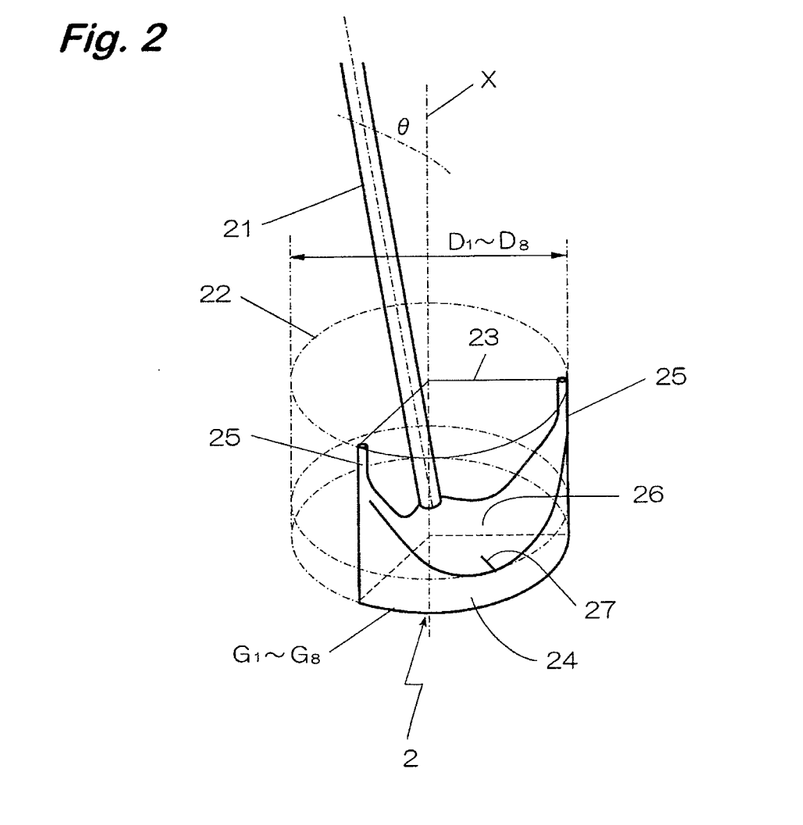
FIG. 2 is an explanatory view showing a valve cusp sizer.

The cusp sizer 2 has a plurality of differently-sized sizer blocks $G_1$ to $G_8$ for measuring the length of the valve annulus from one commissure portion of a valve cusp to a valve annulus to another commissure portion of the valve cusp to the valve annulus of an excised valve cusp, and each of the sizer blocks is attached to each of the top ends of grip members 21, 21, - - - .

Then, as shown in FIG. 2, each of the sizer blocks $G_1$ to $G_8$ has, as a basic shape, a partial circular cylinder 23 formed by cutting different-sized circular cylinder 22 at an angle conforming to the central angle for the commissure portions of the aortic valve (120° in this embodiment, while assuming that the central angles for three commissure portions K are equal).

The outer peripheral surface is formed as an arcuate surface 24 to be abutted against the valve annuls of an aorta from which an abnormal valve cusp has been excised, and contact probe portions 25 of a predetermined length for positioning and abutting both ends of the arcuate surface 24 against the commissure portions K, K are formed in parallel with the central axis of the arcuate surface 24.

The diameter of the circular cylinder 22 (arcuate surface 24) is used as the nominal diameter ($D_1$ to $D_8$) for defining the size of the valve cusp. In this embodiment, sizer blocks $G_1$ to $G_8$ having eight types of nominal diameters $D_1$ to $D_8$ from 17 to 31 mm on every 2 mm step are used while considering the personal differences for the diameter of adult aorta.

Then, numerical values for the nominal diameters $D_1$ to $D_8$ are indented to the grip members 21 such that the size of the sizer block $D_1$ to $D_8$ attached to the top ends thereof can be read.

Further, the central point $P_C$ for the base B of the valve cusp is at a position lower than the bottom end $C_L$ of a coaptation zone (refer to FIG. 11). Therefore, the upper surface 26 for each of the sizer blocks $G_1$ to $G_8$ is formed being curved in a concave shape such that the central point $P_C$ for the base B of the valve cusp between the commissures portions K, K where the valve cusp is to be stitched can be seen when each of the contact probe portions 25 is abutted against each of the commissure portions K, K from which the valve cusp has been excised.

Further, an index 27 as a center marker for defining the central point $P_C$ is formed at a position of the upper surface thereof corresponding to the central point $P_C$ in a case of starting stitching from the central point $P_C$.

Then, the grip member 21 is attached to the center of the partial circular cylinder 23 that forms each of the sizer blocks $G_1$ to $G_8$ such that it does not hinder the observation of the valve annulus in a state of abutting the arcuate surface 24 of each of the sizer blocks $G_1$ to $G_4$ to the valve annulus, and the grip member 21 is inclined by a predetermined angle θ (θ=30°) in this embodiment) relative to the central axis X to the side opposite to the arcuate surface.

Figure 3:
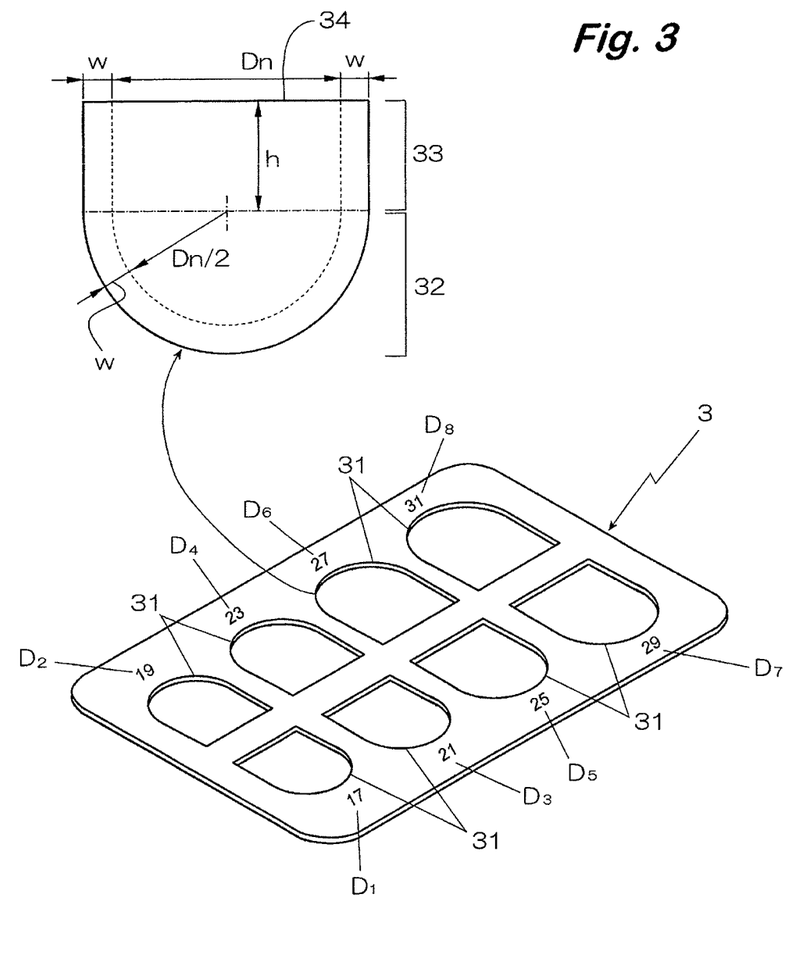
FIG. 3 is an explanatory view showing a template.

FIG. 3 shows the template 3 which is put over the artificial membrane or the biomembrane for scribing the lines of the shape of the valve cusp by using a sterilized surgery skin marker, etc. and in which a plurality of scribing portions 31 having differently-sized shapes of the valve cusp are perforated.

The scribing portion 31 is formed as a semi-circular-rectangular part comprising a substantially semi-circular base forming portion 32 and a substantially rectangular coaptation forming portion 33 in contiguous therewith.

When assuming that a valve cusp sizer 2 is inserted to a valve annulus from which a valve cusp has been excised and that contact probes 25 formed on both ends of the arcuate surface of a sizer block Gn ($G_1$ to $G_8$) conform to both of the commissure portions of the excised valve cusp, the valve cusp base forming portion 32 has a diameter as a sum of the diameter defined as a nominal diameter Dn of the circular cylinder and an allowance for stitching margins 2W on both right and left sides (Dn+2w). The stitching margin is designed as: w=3 mm in this embodiment.

Further, the coaptation zone forming portion 33 is formed as a rectangular shape having a width equal with the diameter of the cusp base forming portion 32 from both ends of the cusp base forming portion 32 to the free margin portion 34 at the top end, and having a length h of 12 mm which is necessary and sufficient as the height for the coaptation zone.

Then, nominal diameters $D_1$ to $D_8$ are described as guide numbers for respective scribing portions 31. Thus, the scribing portion 31 conforming to the measured nominal diameter Dn of the aorta measured by the cusp sizer 2 can be selected easily.

Figure 4:
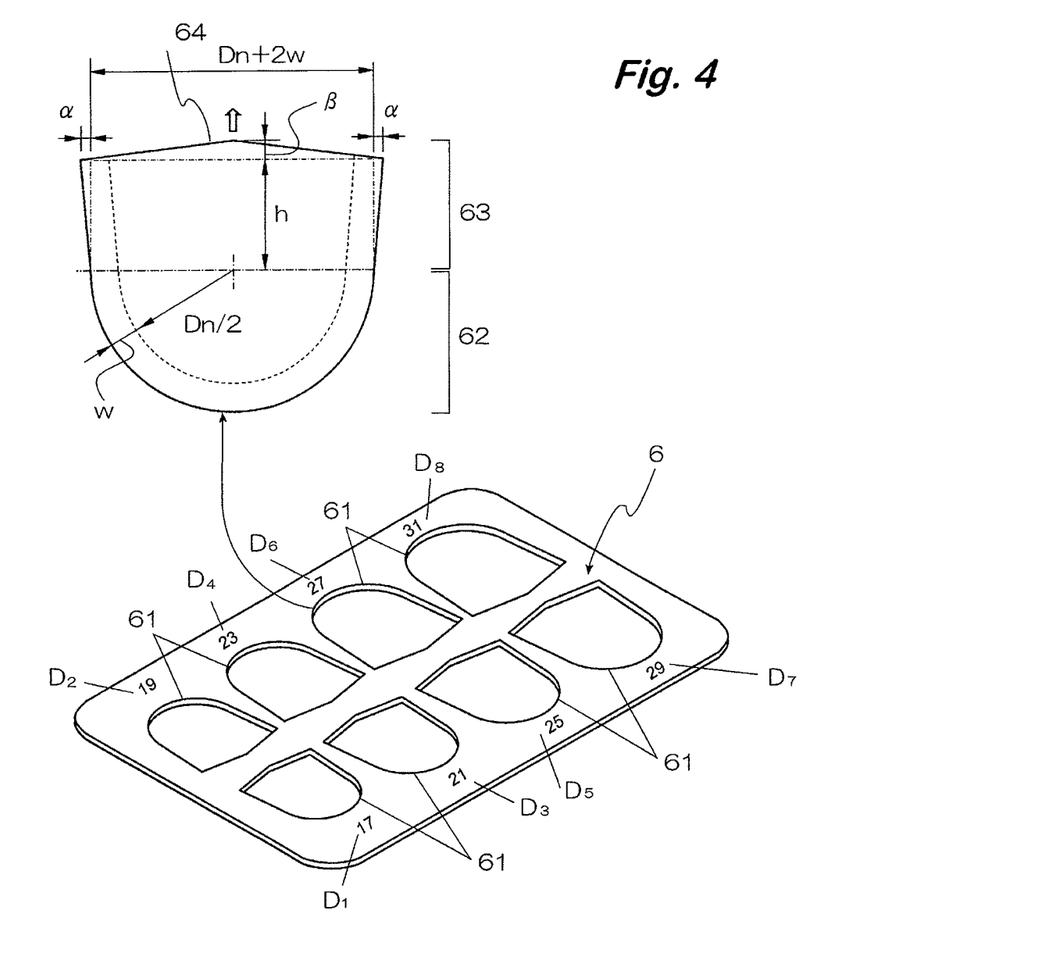
FIG. 4 is an explanatory view showing another embodiment of a template.

FIG. 4 shows another improved template 6, in which the shape of the scribing portions 61 - - - is improved for further decreasing the back flow blood.

This embodiment is identical with the first embodiment in that a cusp base forming portion 62 is formed of a semi-circle having a diameter as a sum of the nominal diameter Dn and an allowance for the stitching margins 2w on both right and left sides (Dn+2w).

A coaptation zone forming portion 63 is formed as a pentagonal shape in which both end edges thereof are extended for a length h conforming to the height of the coaptation till it reaches the free margin 64 at the top end while being gradually widened from both ends of the semi-circular cusp base forming portion 62, and the center of the free margin portion 64 at the top end thereof is protruded into an angled shape.

In this embodiment, the maximum width α of the coaptation zone forming portion 62 is designed as: α=1 mm and the protrusion length β at the center of the free margin portion 64 is designed as: β=2 to 3 mm.

In this embodiment, an allowance is provided for the length of the free margin portion 64 by gradually increasing the width thereof while maintaining the substantially rectangular shape as the coaptation zone forming portion 63, and air tightness is improved when the valve cusps are closed to reliably prevent backflow of the blood by increasing the height for the central portion where three valve cusps are in contact with each other.

Figure 6:
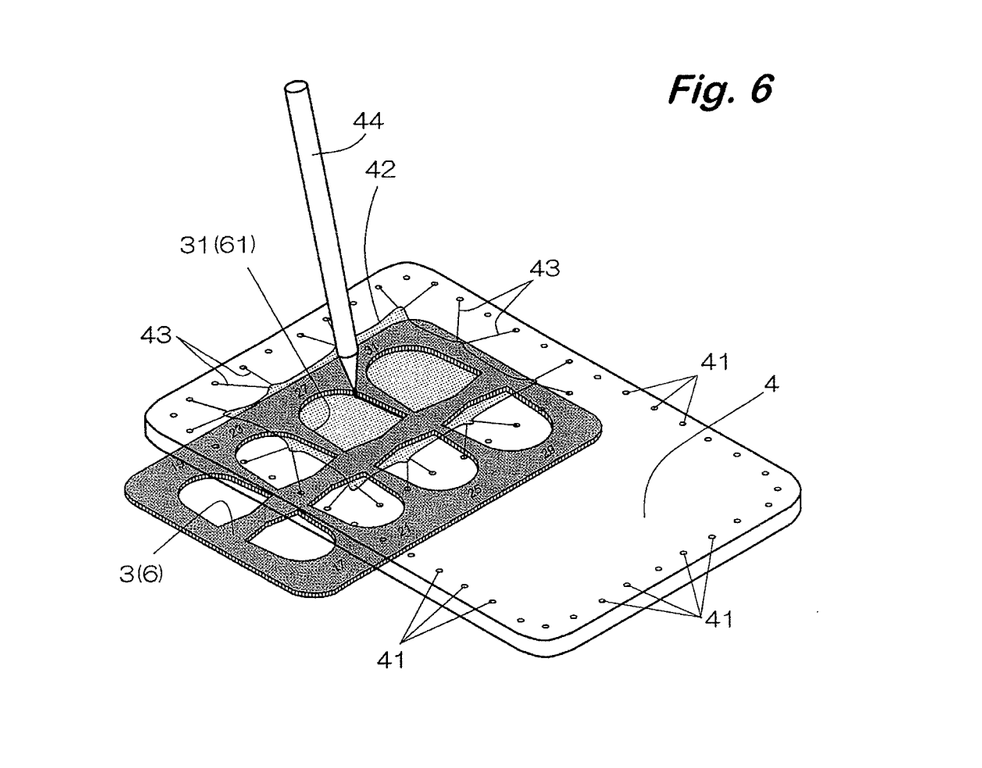
FIG. 6 is an explanatory view showing the template in the state of use.

The base plate 4 is formed, for example, of a stainless steel plate in which perforations 41 are formed at the periphery thereof for putting and stretching threads 43 that are passed through the biomembrane or the artificial membrane (refer to FIG. 1, FIG. 6).

Figure 5A:
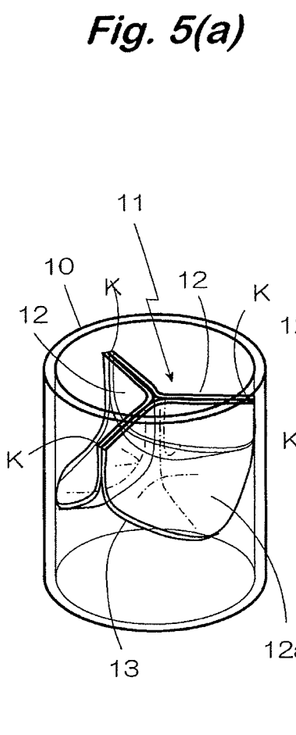
FIG. 5(a) is an explanatory view showing an aortic valve before excising a valve cusp.
Figure 5B:
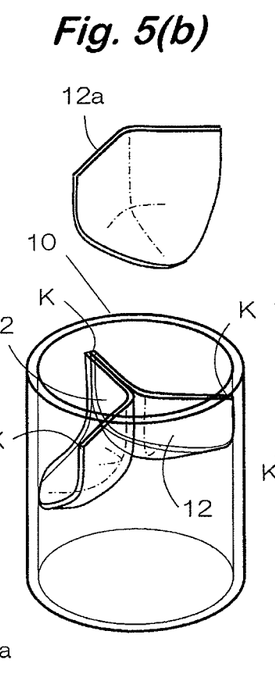
FIG. 5(b) is an explanatory view showing an aortic valve from which a valve cusp has been excised.
Figure 5C:
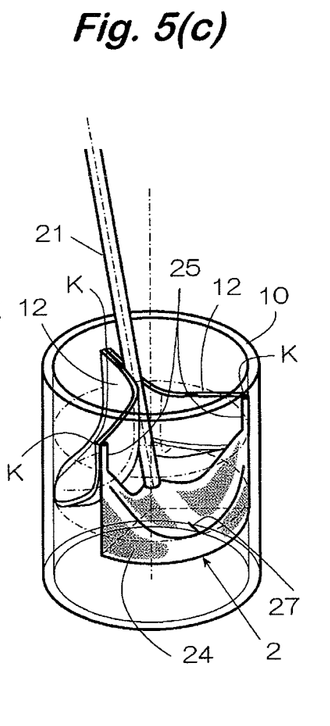
FIG. 5(c) is an explanatory view showing the state of measuring the size of a valve cusp.

The constitution of the embodiment of the present invention is as has been described above and the operation thereof is to be described to an example for the treatment of aortic valve stenosis with reference to FIG. 5 and FIG. 6.

Aortic valve reconstruction is applied, for example, by leaving two valve cusps 12, 12 that can function normally by removing a calcium component by a supersonic surgical aspirator as they are and replacing only one valve cusp 12a that cannot be repaired by decalcification with a prosthetic valve cusp formed of an autoluguous pericardium among three valve cusps 12 of an aortic valve 11 suffering from aortic valve stenosis caused by deposition and calcification of calcium.

In this case, skins, subcutis, and fascia are at first incised to exteriorize sternum, which is subjected to medium sternotomy and then the pericardium is incised. Then, extracorporeal circulation is started by a pump oxygenator in a state of exposing the heart and, after stopping cardiac activity, the aortic valve 11 is exposed on the side of the aorta.

Then, the pericardium is incised into an appropriate size and the pericardium 42 is extended over the base plate 4 and dipped in a histological fixture such as glutaraldehyde in a fixed state by putting around threads 43.

Then, as shown in FIG. 5(a) to (b), among three valve cusps 12, - - - of the aortic valve 11, one valve cusp 12a is excised by applying a surgical knife along the fixing edge 13 thereof, a cusp sizer 2 is inserted to the portion as shown in FIG. 5(c) to measure the size of the excised valve cusp 12a.

Specifically, differently-sized sizer blocks $G_1$ to $G_8$ of the cusp sizer 2 are inserted successively and abutted to the valve annulus of the aorta 10 from which the valve cusp 12a has been excised, and a sizer block Gn in which the contact probe portions 25 disposed on both ends of the arcuate surface 24 thereof conform to both of the commissure portions K, K of the excised valve cusp 12a is confirmed and the nominal diameter Dn for the cusp sizer 2 is read.

When the nominal diameter Dn that determines the cusp size is decided, the pericardium 42 dipped in glutaraldehyde is taken out together with the base plate 4, over which the template 3(6) is placed, and lines for the cusp shape is drawn along the inner peripheral surface of the scribing portion 31 (61) conforming to the nominal diameter Dn on the autoluguous pericardium 42 by a skin marker 44. Then, it is detached from the base plate 4 and cut into the scribed shape by a shear sizer and dipped in physiological saline for preventing drying.

In a case of forming, for example, only one valve cusp, the valve cusp formed of the pericardium 42 may be dipped in a vessel such as a tray or a Petri dish containing physiological saline. However, the tricuspid valve of the aortic valve includes three members of right coronary valve cusp, left coronary valve cusp, and non-coronary valve cusp. In a case of forming two or more of them and if the size of respective cusps are different subtly, when they are happened to be stitched erroneously, this brings about a trouble in the aortic valve reconstruction.

Figure 7:
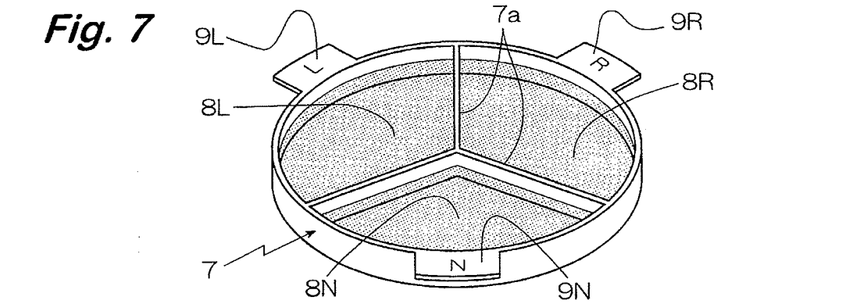
FIG. 7 is an explanatory view showing a petri dish type vessel for preparing each cusp individually.

In order to prevent this, as shown, for example, in FIG. 7, a petri dish type vessel 7 for preparing each cusp individually is used. The vessel is partitioned into three parts of a right coronary cusp dipping portion 8R, a left coronary cusp dipping portion 8L, and a non-coronary cusp dipping portion 8N by partition walls 7a, and identification tags 9R, 9L, 9N are attached for identifying respective dipping portions 8R, 8L, 8N. By filling the respective dipping portions 8R, 8L, 8N with physiological saline and dipping valve cusps formed of the pericardium 42 into respective dipping portions 8R, 8L, 8N, a risk of erroneously stitching them during surgery can be prevented.

Then, when the valve cusp can be formed from the autologous pericardium 42, the cusp sizer 2 having the nominal diameter Dn is again abutted so as to conform the contact probe portions 25 thereof to both commissure portions K, K of the excised valve cusp 12a, a thread is put to a valve annulus at a position indicated by an index 27 formed to a position corresponding to the central point $P_C$ of the base B of the valve cusp with reference to the index 27, the central point $P_C$ of the base B of the valve cusp is stitched and then they are stitched successively toward respective commissure portions K, K with the point Pc as a reference.

Thus, the aortic valve can be reconstructed by stitching a valve cusp formed of the autologuous pericardium to a portion where the valve cusp 12a has been excised.

Since the valve cusp formed as described above is made of the autologuous pericardium, it does not cause rejection. Further, since the valve annulus of the aortic valve can be utilized as it is, no additional valve annulus is formed and projected into the aorta and, accordingly, the pressure loss during opening of the valve is extremely small.

While the description has been made to a case of forming the valve cusp with the pericardium, the present invention can be applied also to a case of forming the valve cusp with a heterogenic biomembranes of animals such as cattle, horses and swinery, as well as with artificial membranes.

INDUSTRIAL APPLICABILITY

As has been described above, the present invention is applicable use of forming a valve cusp of optimal size and shape upon treatment of abnormal valve cusp syndrome by cardiac valve reconstruction of stitching a valve cusp formed of an artificial membrane or a biomembrane to a portion of a tricuspid cardiac valve such as an aortic valve from which an abnormal valve cusp has been excised.

DESCRIPTION OF THE REFERENCES 1 valve cusp forming instrument
2 valve cusp sizer
3 template
$G_1$ to $G_8$ sizer block
21 grip member
22 circular cylinder
24 arcuate surface
25 contact probe portion
31 scribing portion
32 valve cusp base forming portion
33 coaptation zone forming portion
$D_1$ to $D_8$ nominal diameter

What is claimed is:

1. A method of treatment of abnormal valve cusp syndrome, the method comprising:
    excising one or two abnormal valve cusps selected from the group of left coronary cusp, right coronary cusp and noncoronary cusp, without excising a remaining valve cusp or valve cusps that can function normally;
    inserting a cusp sizer at a portion where the one or two abnormal valve cusps are excised,
wherein the cusp sizer comprises a sizer block with an arcuate surface with an angle conforming to the central angle for commissure portions of an aortic valve, the arcuate surface comprising two probe portions disposed on both ends thereof;
    an upper surface of the sizer block being curved in a concave shape and comprising an index which is a center marker for defining a central point from which stitching is started;
    measuring the size of the excised valve cusp or valve cusps by:
    making the sizer block abut the valve annulus of an aorta from which the valve cusp or valve cusps are excised, the central point for the base of the valve cusp between the commissure portions being visible;
    confirming the two probe portions of the sizer block fit to both of the commissure portions of the excised valve cusp or one of the excised two abnormal valve cusps, thereby reading nominal diameter of the cusp sizer;
    obtaining a new valve cusp formed of a pericardium by:
    scribing lines for a cusp shape by drawing along an inner peripheral surface of a scribing portion of a template which relates to the nominal diameter to the pericardium; and
    cutting the pericardium in accordance with the lined cusp shape;
    dipping the new valve cusp formed of a pericardium in saline;
    abutting the cusp sizer having the nominal diameter in a manner that the two commissure portions of the excised valve cusp conforms to the two probe portions of the sizer block;
    putting a thread to a valve annulus at a position indicated by the index;
    stitching the central point of the base of the valve cusp; and
    stitching toward the commissure points from the central point, thereby reconstructing the aortic valve.

2. The method in accordance with claim 1,
wherein dipping the new valve cusp comprises dipping the new valve cusp in one of a left coronary cusp dipping portion, right coronary cusp dipping portion and a noncoronary cusp dipping portion of a vessel,
the left coronary cusp dipping portion comprising an identification tag of the left coronary cusp dipping portion;
the right coronary cusp dipping portion comprising an identification tag of the right coronary cusp dipping portion; and
the noncoronary cusp dipping portion comprising an identification tag of the noncoronary cusp dipping portion.

3. The method in accordance with claim 1,
wherein obtaining the new valve cusp comprises obtaining the new valve cusp by:
lining for a cusp shape by drawing along an inner peripheral surface of a scribing portion of a template which relates to the nominal diameter to the pericardium,
the inner peripheral surface of the scribing portion comprising:
an inner peripheral surface of a valve cusp base forming portion of the template which has a diameter as a sum of a diameter defined as the nominal diameter and an allowance for stitching margins; and
an inner peripheral surface of a coaptation zone forming portion in which both end edges thereof are extended in a manner that the portion is gradually widened from both ends of the valve cusp base forming portion angled shape portion of the template to a free margin portion thereof, and a center of the free margin portion being protruded at the top end thereof and having an angled shape.

* * * * *